(12) United States Patent
List (10) Patent No.: US 8,172,866 B2
(45) Date of Patent: May 8, 2012

(54) MEDICAL AID

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 511 days.

(21) Appl. No.: 12/397,092

(22) Filed: Mar. 3, 2009

(65) Prior Publication Data

US 2010/0056893 A1 Mar. 4, 2010

Related U.S. Application Data

(63) Continuation of application No. PCT/EP2007/059024, filed on Aug. 30, 2007.

(30) Foreign Application Priority Data

Sep. 4, 2006 (EP) .................................... 06120063

(51) Int. Cl.
*A61B 5/00* (2006.01)

(52) U.S. Cl. ........................................ 606/181; 600/583

(58) Field of Classification Search .................. 606/181, 606/183; 600/583
See application file for complete search history.

(56) References Cited

U.S. PATENT DOCUMENTS

| | | | |
|---|---|---|---|
| 4,442,836 A | 4/1984 | Meinecke et al. | |
| 5,286,362 A | 2/1994 | Hoenes et al. | |
| 5,554,166 A | 9/1996 | Lange et al. | |
| 6,520,326 B2 | 2/2003 | McIvor et al. | |
| 7,223,248 B2 * | 5/2007 | Erickson et al. | 600/584 |
| 7,374,546 B2 | 5/2008 | Roe et al. | |
| 7,481,777 B2 | 1/2009 | Chan et al. | |
| 7,976,479 B2 * | 7/2011 | List | 600/584 |
| 2003/0153939 A1 | 8/2003 | Fritz et al. | |
| 2003/0211619 A1 | 11/2003 | Olson et al. | |
| 2004/0163987 A1 * | 8/2004 | Allen | 206/438 |

(Continued)

FOREIGN PATENT DOCUMENTS

CA 2 050 677 3/1992

(Continued)

OTHER PUBLICATIONS

PCT/EP2007/059024 International Preliminary Report on Patentability/Written Opinion mailed Mar. 19, 2009.

(Continued)

*Primary Examiner* — Max Hindenburg
*Assistant Examiner* — Michael C Stout
(74) *Attorney, Agent, or Firm* — Woodard, Emhardt, Moriarty, McNett & Henry LLP (57) ABSTRACT

The invention relates to a medical aid which comprises a lancet. The lancet is at least partially enclosed by a packaging that comprises a flexible film section. The lancet is arranged displaceably between upper and lower protective sections of the packaging. The flexible film section is detachably connected, along at least one segment of its first and second lateral edges, to an additional flexible film section or one of the protective sections. The flexible film section is connected to an additional flexible film section or one of the protective sections near the lancet tip via a detachable connection to enclose the lancet tip in the packaging. The proximal ends of the lower and upper protective sections can be bent apart to create an opening in the packaging at the detachable connection through which part of the lancet is pushed out from the packaging in the proximal direction.

12 Claims, 2 Drawing Sheets

U.S. PATENT DOCUMENTS

| | | |
|---|---|---|
| 2005/0036909 A1* | 2/2005 | Erickson et al. ............... 422/61 |
| 2006/0079810 A1 | 4/2006 | Patel et al. |
| 2006/0247555 A1* | 11/2006 | Harttig ........................ 600/584 |
| 2007/0016103 A1* | 1/2007 | Calasso et al. ............... 600/583 |
| 2007/0038150 A1 | 2/2007 | Calasso et al. |
| 2008/0065131 A1* | 3/2008 | List ............................. 606/181 |
| 2008/0103415 A1 | 5/2008 | Roe et al. |

FOREIGN PATENT DOCUMENTS

| | | |
|---|---|---|
| EP | 0 299 517 B1 | 6/1993 |
| EP | 0 678 308 B1 | 10/1995 |
| EP | 0 748 183 B1 | 12/1996 |
| EP | 1 360 935 A1 | 11/2003 |
| EP | 1 492 457 B1 | 1/2005 |
| EP | 1 508 304 A1 | 2/2005 |
| GB | 1099920 | 1/1968 |
| WO | WO 98/48695 A1 | 11/1998 |
| WO | WO 01/066010 A1 | 9/2001 |
| WO | WO 2004/075760 A1 | 9/2004 |
| WO | WO 2005/084530 * | 9/2005 |
| WO | WO 2005/104948 A1 | 11/2005 |
| WO | WO 2007/147494 A2 | 12/2007 |

OTHER PUBLICATIONS

PCT/EP2007/059024 International Preliminary Report on Patentability/Written Opinion Translation mailed Mar. 26, 2009.

International Application PCT/EP2007/059024 International Search Report mailed Feb. 14, 2008.

* cited by examiner

MEDICAL AID

CROSS REFERENCE TO RELATED APPLICATION

This application is a continuation of International Application No. PCT/EP2007/059024, filed Aug. 30, 2007, which claims the benefit of European Application No. 06 120 063.0, filed Sep. 4, 2006, the entire disclosures of which are hereby incorporated by reference.

BACKGROUND

The invention relates to a medical aid comprising a lancet and to a sensor comprising a test element, the lancet or the test element being at least partially enclosed by a (preferably flexible) packaging.

In clinical diagnostics, examination of blood samples or of interstitial fluid permits early and reliable detection of pathological conditions and also specific and reliable monitoring of physical states. Medical diagnostics always entails obtaining a sample of blood or of interstitial fluid from the individual who is to be examined.

To obtain the sample, the skin of the person to be examined can be punctured, for example at the finger pad or ear lobe, with the aid of a sterile, sharp lancet, in order in this way to obtain a few microliters of blood for the analysis. This method is particularly suitable for sample analysis that is carried out directly after the sample has been obtained.

In the area of home monitoring in particular, in other words where persons without specialist medical training carry out simple analyses of blood or of interstitial fluid themselves, and particularly for diabetics taking blood samples on a regular basis, several times a day, to monitor their blood glucose concentration, lancets and associated devices (puncturing aids) are sold that allow samples to be taken with the least possible discomfort and in a reproducible manner. Such lancets and devices (puncturing aids) are the subject matter of, for example, WO-A 98/48695, U.S. Pat. No. 4,442,836 or U.S. Pat. No. 5,554,166.

Self-monitoring of blood glucose levels is a method of diabetes control that is nowadays applied worldwide. Blood glucose monitors in the prior art comprise an analysis device into which a test element (test strip) is inserted. The test element is brought into contact with a droplet of a sample which has previously been obtained by means of a puncturing aid, for example from the pad of a finger.

The prior art also includes numerous test elements, and sensors comprising such test elements, which can be used to determine the concentration of at least one analyte (for example glucose, lactate or cholesterol) in the liquid sample, particularly in blood or interstitial fluid. These test elements or sensors can be based, for example, on electrochemical measurement methods, such as are described in U.S. Pat. No. 5,286,362, for example. Other test elements and sensors are based, for example, on an optical detection of the at least one analyte. The analyte can thus react in particular with a detection reagent contained on or in the test element, in which case the test element (for example a test area of the test element) changes at least one measurable optical property (e.g. a color, a fluorescence, a reflectivity, or a combination of these properties). The change in this property can be optically detected, in order to determine from this the concentration of the at least one analyte. Illustrative embodiments of test elements or sensors of this kind, designated hereinbelow also as "optical test elements", are known from CA 2,050,677, for example.

Test elements and sensors are also known that are packaged in such a way that a magazine comprises several such test elements. For example, several test elements or sensors can be received on an analysis tape. Examples of analysis tapes comprising a plurality of test areas are disclosed in EP 0 299 517 B1.

Sensors and test elements are also known which are not designed for single, brief contact with the sample but are instead configured so as to remain in the sample for a longer measurement period, for example for a few hours, days or weeks. An important use of sensors of this kind is in the field of implantable sensors, for example subcutaneous sensors, which can be implanted under a patient's skin (for example in the interstitial fatty tissue). These sensors are generally designed for continuous monitoring of the analyte concentration, or for monitoring of the analyte concentration at short intervals, and are able to exchange data with a measurement device, for example via an electrical connection. Examples of implantable sensors or test elements of this kind, based on an electrochemical measurement principle, are given in EP 0 678 308 B1 or in EP 0 748 183 B1. Both documents describe not only the actual structure of the sensor but also an insertion aid by means of which the sensor can be implanted. After the implantation, the insertion aid can be removed again from the skin area.

The numerous system components (lancet, puncturing aid, test element and analysis device) require a lot of space and involve quite complex handling. Systems have also been developed which have a greater degree of integration and are thus easier to handle and in which, for example, the test elements are stored in the analysis appliance and made available for the measurement. A further step in terms of miniaturization will be achieved, for example, by integrating several functions or function elements within a single analytical aid (disposable). For example, the operating sequence can be greatly simplified by suitable combination of the puncturing procedure and of the detection of the analyte concentration by means of a sensor on a test element.

In the prior art, it is known to provide the lancets of such analytical aids with a capillary structure or to make them part of a capillary structure (for example from WO 2005/104948 A1). There, after the skin has been punctured and the sample emerges, the lancet tip is brought into contact with the sample in order to collect the latter with the capillary.

The lancet tip of lancets used for blood extraction is typically sterilized in advance and kept in a sterile state by a sterile protector (for example in the form of a cap or pocket) before being used for a puncturing procedure, in order to ensure that the lancet tip is not contaminated by its surroundings. Moreover, measures are often taken to ensure that, after the skin has been punctured, the lancet tip is shielded again (if appropriate by means of the same cap or pocket), such that accidental injuries and associated infections caused by blood adhering to the lancet tip are avoided.

In the case of individual lancets, a sterile protector can be produced, for example, by the lancet tip being encapsulated with plastic by injection molding in one operation together with the production of the lancet body. Before use, the user removes this part manually, generally upon insertion into a puncturing aid. In the case of lancets encased in a magazine, similar sterile protection devices are customary, for example devices in which the lancet is pulled to the rear out of a sterile protector, whereupon the sterile protector is conveyed out of the puncturing path by spring force. Relatively complicated mechanisms, in particular springs that are integrated in the equipment, are required for this.

WO 01/66010 circumvents the complicated nature of this mechanism by means of the sterile protector simply being pierced. WO 01/66010 relates to a lancet that comprises a lancet needle with a tip, and a lancet body that completely surrounds the lancet needle at least in the region of the tip. At least in the region of the tip of the lancet needle, the lancet body is made of an elastic material in which the tip of the lancet needle is embedded. Furthermore, a lancet is described which comprises a lancet needle with a tip and a hollow body that surrounds at least the tip of the lancet needle. The lancet needle is movable in the region of its tip in the hollow body, and the hollow body is made at least partially of an elastic material which can be pierced through by the tip of the lancet needle during the puncturing procedure and which, if appropriate, closes again after the tip of the lancet needle is pulled back into the hollow body.

EP 1 360 935 A1 relates to a tape-like package for a large number of medical aids. The aids are accommodated in depressions in a first tape section that are covered by a second tape section.

EP 1 492 457 B1 relates to an automatically opening package for medical aids that comprises the following:
an upper flexible sheet section which has a distal end, a proximal end, a first peripheral edge and a second peripheral edge,
a lower flexible sheet section which has a distal end, a proximal end, a first peripheral edge and a second peripheral edge,
wherein the upper and lower flexible sheet sections are designed such that they can be detachably sealed together along at least one segment of their first and second peripheral edges, as a result of which a medical device is enclosed within the upper and lower flexible sheet sections. A collar is mounted on the distal end of the upper flexible sheet section and on the distal end of the lower flexible sheet section, said collar being mounted on the distal ends of the lower and upper flexible sheet sections in such a way that a relative movement of the collar and of the proximal ends of the upper and lower flexible sheet sections that decreases a distance between them causes the upper and lower flexible sheet sections to pull apart. In this way, the package is automatically opened and at least one section of the medical device is exposed. One disadvantage of this automatically opening package is that the lancet tip is arranged in the area of the package that is pulled back with the movement of the collar. This creates the risk of the lancet tip hitting one of the flexible sheet sections or the seam between the two flexible sheet sections. It can then pierce one of the flexible sheet sections and, as the package is opened further, can be bent by the pulling apart of the sheet portions. Moreover, the lancet tip may hit a seam whose mechanical action or adhesive can adversely alter the surface properties of the lancet tip. If the lancet tip has a capillary structure, it must be hydrophilic, for example in order to ensure that the blood transport functions. Its hydrophilic nature is threatened by contact between the lancet tip and the seam of the package.

SUMMARY

The object of the present invention is therefore to avoid the disadvantages of the prior art and, in particular, to make available a medical aid with a lancet or a sensor with at least one test element which ensure sterile packaging of the lancet or of the test element and whose opening mechanism does not endanger the functionality of the lancet or of the test element.

According to the invention, this object is achieved by a medical aid according to claim 1 and by a sensor according to claim 12, the common basic concept in both cases lying in a suitable design of the packaging.

A medical aid is proposed that comprises a lancet with a proximal end and a distal end, the lancet having a lancet body and, at the proximal end, a lancet tip. The lancet is at least partially enclosed by a packaging that comprises at least one flexible film section having a distal end, a proximal end, a first lateral edge and a second lateral edge. The lancet, at least partially enclosed by the packaging, is arranged displaceably between an upper protective section and a lower protective section. The at least one flexible film section is detachably connected, along at least one segment of its first and second lateral edges, to an additional flexible film section or to one of the protective sections. The at least one flexible film section is further connected to an additional flexible film section or to one of the protective sections in the area of the lancet tip via a detachable connection, such that the lancet tip is enclosed by the packaging. The at least one flexible film section is further connected to one of the protective sections via a fixed connection at a distance from the detachable connection. The proximal ends of the lower and upper protective sections can be bent apart, as a result of which the distance between the detachable connection and the fixed connection is increased and a tensile force is thus applied to the detachable connection, such that the packaging is opened at the detachable connection and a proximal opening is created without the lancet tip having to pierce through the packaging. At least part of the lancet can be pushed out from the packaging in the proximal direction through the proximal opening.

The invention relates in particular to a medical aid comprising a lancet with a proximal end and a distal end, the lancet having a lancet body and, at the proximal end, a lancet tip, and the lancet being at least partially enclosed by a flexible packaging. The flexible packaging comprises an upper flexible film section having a distal end, a proximal end, a first lateral edge and a second lateral edge. The flexible packaging further comprises a lower flexible film section having a distal end, a proximal end, a first lateral edge and a second lateral edge. The upper and lower flexible film sections are detachably connected to each other along at least one segment of their first and second lateral edges and at least partially enclose the lancet. The lancet, at least partially enclosed by the flexible packaging, is arranged displaceably between an upper protective section and a lower protective section. The lower flexible film section and the upper flexible film section are detachably connected to each other via a proximal seam, as a result of which the lancet tip is enclosed by the flexible packaging. In this context, a seam is a connecting line that lies between the two interconnected flexible film sections and that can be produced by any connecting technique known to a person skilled in the art, in particular by sealing or adhesive bonding. The proximal end of the lower flexible film section is fixedly connected to the lower protective section and the proximal end of the upper flexible film section is fixedly connected to the upper protective section. The proximal ends of the lower and upper protective sections can be bent apart in order to open the flexible packaging at the proximal seam, without the lancet tip having to pierce through the flexible packaging. Thereafter, at least part of the lancet can be pushed out from the flexible packaging and from the protective sections in the proximal direction.

A medical aid in this context is in particular a lancet device or a puncturing aid for collecting a sample by puncturing the skin, or an analytical aid that combines the functions of puncturing the skin and collecting a sample or combines the functions of puncturing the skin, collecting a sample and providing test chemicals for analysis of the sample.

In the context of the invention, the proximal end of a component of the analytical aid is in each case the end of the component directed as lancet tip toward the patient's skin. The distal end is the end of the component remote from the proximal end.

The lancet tip of the lancet in the aid according to the invention is used to puncture a patient's skin in order to collect a blood sample or a sample of interstitial fluid. The lancet is at least partially enclosed by the (preferably flexible) packaging, with the packaging enclosing at least the lancet tip in order to protect the latter in the unused state and preferably keep it sterile until directly before use.

The packaging comprises at least one flexible film section. According to a preferred embodiment of the present invention, it is a flexible packaging comprising an upper flexible film section and a lower flexible film section.

In this context, flexible means that the film sections are foldable and, when the packaging is being opened, are so pliable that they can move away from the lancet tip under the action of a slight force. For the flexible film sections or the flexible packaging, a material is preferably used which can be easily bonded, which is not damaged (in particular not made brittle) by a suitable method of sterilization of the lancet and which does not give off any substances that ought not to come into contact with the patient's skin or an opening in the skin. The material of the flexible film sections or of the flexible packaging is preferably a polymer, in particular PET, PP or styrene, paper or metal, in particular aluminum, stainless steel or tin. A flexible film section or a flexible packaging made of a polymer film preferably has a thickness in the range of 3 to 100 µm, particularly preferably of 5 to 15 µm. A flexible film section or a flexible packaging made of paper is preferably produced from the paper used for the blister packaging of disposable syringes. A flexible film section or a flexible packaging made of paper preferably has a thickness in a range of 50 to 150 µm, particularly preferably of ca. 100 µm. For a flexible film section or a flexible packaging made of metal, a metal is preferably used that does not give off any ions to the lancet. A flexible film section or a flexible packaging made of metal preferably has a thickness in a range of 30 to 70 µm, particularly preferably of 50 µm.

In the preferred embodiment with a flexible packaging, the upper and lower flexible film sections form a film pouch enclosing at least part of the lancet, since they are connected to each other at their lateral edges, at the proximal seam and at their distal ends. The proximal ends of the two flexible film sections protrude beyond the proximal seam and are each fixedly connected to an adjoining protective section.

In the context of the present invention, fixedly connected means that the fixed connection does not come undone under the effect of the forces that arise during opening of the packaging and pushing out of the lancet. In contrast to the fixed connection, the detachable connection is configured in such a way (e.g. adhesively bonded, sealed, etc.) that it comes undone during the opening of the packaging.

The two protective sections are more rigid than the flexible film sections in order to ensure that, during the displacement of the lancet, they permit this relative movement, hold the proximal ends of the flexible film sections secure and, before and after use, provide protection for the lancet, for example against pressure or kinking. The lancet is arranged between the upper and lower protective sections such that it does not protrude beyond the proximal ends of the protective sections before the flexible packaging is opened.

According to one embodiment of the present invention, the packaging comprises only one flexible film section, which is connected to one of the protective sections along its lateral edges. The lancet is in this case arranged between the flexible film section and the protective section and is at least partially enclosed by these. The proximal end of the flexible film section is connected to one of the two protective sections (e.g. the upper one) via a detachable connection. From there, the flexible film section extends transversely in front of the lancet tip to the other of the two protective sections (e.g. the lower one), where it is connected to the other protective section (e.g. the lower one) via a fixed connection in the area of the lancet tip. The rest of the flexible film section flanks the lancet and can be fixedly connected at its distal end to one of the two protective sections (e.g. the upper one) in order to enclose at least part of the lancet. In this case, the packaging of the lancet is therefore formed by the flexible film section and by one of the protective sections.

In the present invention, in order to open the (optionally flexible) packaging, the proximal ends of the protective sections are bent apart from each other (preferably elastically). The bending apart can be achieved by bending both protective sections in opposite directions or by bending one of the two protective sections away from the other one, while the other one remains rigidly in its position. Consequently, one of the two protective sections is preferably elastically deformable in order to permit bending of its proximal end, while the other one is either also elastically deformable (at least at the proximal end) or more rigid.

In the preferred embodiment of the present invention already described, with a flexible packaging composed of two flexible film sections that have a proximal connecting seam in front of the lancet tip, the proximal ends of the flexible film sections that are secured fixedly to the two protective sections are pulled apart from each other as a result of the increase in the distance between the protective sections as their proximal ends are bent apart, such that the detachable connection between the flexible film sections at the proximal seam is undone by the force acting on it. A proximal opening thus forms in the flexible packaging in the area of the proximal seam. The lancet (starting with the lancet tip) can be pushed out from the flexible packaging through this proximal opening, in which process it moves in the proximal direction relative to the protective sections until the lancet tip protrudes beyond the proximal ends of the protective sections and can be used to puncture the skin in order to collect a sample.

In the embodiment of the present invention already described, with only one flexible film section which, in the area of the lancet tip, is connected fixedly to one protective section and connected detachably to the other protective section, the proximal end of the flexible film section is pulled away from the protective section as a result of the increase in the distance between the protective sections and thus also between the fixed connection and detachable connection as the two protective sections are bent apart, such that the detachable connection between the proximal end of the flexible film section and the protective section is undone by the tensile force acting on it. A proximal opening thus forms in the packaging in the area of the detachable connection. The lancet (starting with the lancet tip) can be pushed out from the packaging through this proximal opening, in which process it moves in the proximal direction relative to the protective sections until the lancet tip protrudes beyond the proximal ends of the protective sections and can be used to puncture the skin in order to collect a sample.

According to the invention, the proximal opening in the packaging is obtained exclusively by the bending apart of the two protective sections, without the lancet tip being used to open the (preferably flexible) packaging, in particular without the lancet tip piercing the packaging.

As the lancet is being pushed out from the (preferably flexible) packaging through the proximal opening, the packaging can automatically open further, in particular at the lateral edges of the at least one flexible film section, because the at least one flexible film section remains connected to the protective sections via the fixed connection(s), the lancet moves relative to the protective sections and thus also relative to the fixed connection of the at least one flexible film section and additionally widens from the lancet tip to the lancet body.

The distal ends of the at least one flexible film section are preferably connected fixedly to the distal end of the lancet, such that they move together with the lancet and cause the lancet to "peel out" of the flexible packaging upon displacement of the lancet relative to the protective sections and relative to the fixedly connected areas of the film sections.

After use, the lancet tip can be pulled back again completely between the two protective sections, such that the user is protected against accidental further puncturing of the skin. The retracted lancet is preferably covered again on both sides by the (preferably flexible) packaging.

One of the advantages of the medical aid according to the invention is that the (preferably flexible) packaging, which preferably serves as a sterile protector for the lancet, opens substantially automatically, without the lancet tip being damaged and without the user being exposed to a risk of unintentional puncturing by the lancet tip. The sterile protector is opened without the need for complicated or awkward handling of the medical aid. The simple design of the medical aid also permits inexpensive production, in particular inexpensive mass production. Before use, the protective sections protect the lancet from damage, and the packaging protects it from contamination. The protective sections also protect the user from inadvertent contact with the lancet tip.

The invention further relates to a method for unpacking the medical aid, said method comprising the steps of:
  bending the proximal ends of the lower and upper protective sections apart, as a result of which the packaging is opened at the detachable connection, such that a proximal opening is created, and
  pushing at least part of the lancet out from the (preferably flexible) packaging and from the protective sections in the proximal direction through the proximal opening, such that at least the lancet tip protrudes beyond the proximal ends of the protective sections.

The advantages and details of this method have already been explained in connection with the medical aid according to the invention. In particular, the bending apart can be achieved, for example, by bending both protective sections in opposite directions or by bending one of the two protective sections away from the other one, while the other one remains rigidly in its position.

In the context of the present invention, a lancet is a puncturing instrument that is suitable for perforating a patient's skin. For example, it can be a solid, needle-shaped body. A further example of a lancet within the meaning of the present invention is the needle of the subcutaneous glucose sensor kit known from U.S. Pat. No. 6,520,326 B2.

According to a preferred embodiment of the present invention, the lancet has a capillary structure formed by a half-open channel. The capillary structure serves to take up a sample after a puncturing procedure, the sample being able to be taken up by capillary forces into the hydrophilic capillary structure. Since the (preferably flexible) packaging is opened without involvement of the lancet tip, it is possible to avoid damaging or contaminating the capillary structure or adversely affecting its surface properties.

According to a preferred embodiment of the present invention, the medical aid cooperates with a driver element which engages through at least one of the protective sections, is connected to the lancet body and can be displaced together with the lancet in the proximal direction relative to the protective sections. According to another preferred embodiment of the present invention, the medical aid comprises a driver element which engages through at least one of the protective sections, is connected to the lancet body and can be displaced together with the lancet in the proximal direction relative to the protective sections. In both cases, the driver element serves to push the lancet at least partially out from the (preferably flexible) packaging and from the protective sections, either automatically, by means of a dedicated component of an analysis system or of a puncturing aid, or manually by a user. For this purpose, the protective sections can be held securely (e.g. by the user) and the driver element displaced relative to the protective sections, or the driver element is held securely and the protective sections are displaced relative to the driver element. For this purpose, at least one of the protective sections preferably has a recess through which the driver element slides and is guided during its displacement.

According to a preferred embodiment of the present invention, the lancet is displaced automatically between the protective sections. For this purpose, the medical aid, or a puncturing device comprising the medical aid, has a driven ram, for example, which acts in the proximal direction directly on the distal end of the lancet or acts on the lancet body via a driver element at another position.

In the medical aid according to the invention, in the embodiment with an upper flexible film section and a lower flexible film section, the lancet body at the distal end of the flexible packaging can be adhesively bonded into the flexible packaging. In the medical aid according to the invention, in the embodiment with only one flexible film section, the distal end of the lancet body can be adhesively bonded between the flexible film section and one of the protective sections.

In the already described embodiment of the invention with a flexible packaging, the upper and lower flexible film sections are preferably sections of a single flexible film which is bent back at the distal ends of the flexible film sections. The flexible film in this case is, for example, folded about the distal end of the lancet body such that an upper flexible film section and a lower flexible film section are formed. These two flexible film sections can then be connected detachably to each other along their lateral edges and transversely in front of the lancet tip, for example by sealing or adhesive bonding, in order to serve as a flexible packaging that completely encloses the lancet.

In the present invention, the (preferably flexible) packaging can enclose or cover a part of the lancet, the whole lancet or other components of the medical aid (for example parts of a driver element) in addition to a part of the lancet or the whole lancet.

According to a preferred embodiment of the present invention, the proximal end of one of the protective sections of the medical aid according to the invention has, on its inside, a test area, which is provided for analysis of a sample. For this purpose, at least one of the protective sections can be sufficiently extended in the proximal direction, in relation to the at least one flexible film section or the flexible packaging, in order to include the test area on its inner face within the extended region. For analysis purposes, a sample is transported into the test area, where it may react with one or more reagents before being analyzed. The analysis can be performed optically, in particular photometrically, or electrochemically. For photometric analysis, the test elements contain a reagent system, the reaction of which with the analyte leads to a photometrically detectable change (a change in color). The reagents are in this case usually located in a test area of the test element, the color thereof changing as a function of the concentration. This change in color can be determined quantitatively by reflection photometry with the aid of a measuring arrangement.

Electrochemical test elements contain an electrochemical reagent system, the reaction of which with the analyte influences the electric voltage between two poles of the test element and/or the current intensity flowing between two poles of the test element at a defined voltage. In this case, therefore, the voltage or current intensity is the physically measurable variable which is determined by a corresponding measuring arrangement, integrated in the analysis system and designed as a voltage or current measurement device, and whose change correlating with the concentration of the analyte is converted into the analysis data (concentration of the analyte).

In the medical aid according to the invention, the protective section carrying the test area can be made transparent, at least in the region of the test area, such that an analysis system provided for this purpose can perform a photometric analysis of a sample on the test area, in which case light from a light source can pass through the transparent region onto the test area and, reflected from this, can once again pass through the transparent region to a detector.

In this embodiment of the medical aid according to the invention, the sample is preferably applied to the test area arranged on the inside at the proximal end of one of the protective sections, by means of the sample being taken up in a capillary structure formed by a half-open channel of the lancet and by means of the sample being scraped off onto the test area. For this purpose, for example, a user can actively press the test area against the capillary structure with the sample contained therein, after the lancet has been retracted to the appropriate position.

It is also possible, however, for a capillary structure to be provided on or in the protective section carrying the test area, which capillary structure transports the sample by capillary forces from a sample application site on the protective section to the test area. Direct application of the sample to a test area is also possible if the test area is arranged in an exposed position on the protective section.

According to one embodiment of the present invention, the distal ends of the protective sections are connected to a holding element that comprises a spacer piece, by means of which the distal ends of the protective sections are held at a defined distance from each other. In the present invention, the protective sections are preferably two rectangular sections (for example of film or paper) which are arranged with their distal ends at a defined distance from each other (preferably parallel to each other in a rest position prior to use) and which, at least at their proximal ends, have a suitably wide opening through which the lancet can be pushed at least partially out. To ensure that the protective sections can be kept at the fixed distance, a holding element with a spacer piece is provided, for example. A user can also grip the medical aid at the holding element during use.

As has been explained above, the basic concept of the invention, namely that of providing a sterile packaging that avoids the disadvantages of the sterile packages known from the prior art, can also be applied to other medical or chemical devices. It is proposed in particular that this basic concept be applied to a sensor for detection of at least one analyte in a sample. The at least one analyte can be glucose, for example, or another analyte, in particular a metabolite, for example cholesterol, lactate or other types of analytes. In particular, the sample can be a liquid sample, in particular a body fluid such as blood or interstitial fluid.

The proposed sensor comprises at least one test element suitable for the detection of the at least one analyte (qualitative and/or quantitative detection being possible). This test element can correspond, for example, to one of the test elements described at the outset and known from the prior art and can, for example, perform an electrochemical and/or optical detection of the analyte. For example, the test element can be strip-shaped, tube-shaped or of some other configuration. The sensor can comprise one or more such test elements and can, for example, perform only a storage function for the test elements or, alternatively or in addition to this, it can also comprise control and evaluation electronics and/or an optical system. For the design of the sensors, reference may be made in particular to the implantable sensors set forth in EP 0 678 308 B1 and EP 0 748 183 B1, where the packaging described below can completely or partially enclose not only the actual flexible sensor (which corresponds to the test element) but also, for example, component parts of the insertion unit, for example the hollow insertion needle. Thus, it is particularly preferable for those parts of the test element and/or the parts of the sensor in direct contact with body fluid or body tissue, i.e. parts implanted at least temporarily, to be at least partially enclosed by the packaging. The proximal end of the test element should therefore include the implanted parts. Other component parts, in particular component parts remaining outside the body tissue, can also remain outside of the packaging. In particular, the test element can comprise a test chemical, for example, to which liquid is guided by a capillary structure or a similar fluidic structure, which test chemical is not implanted in the body. In this case, the test chemical can also remain outside the body. Application to other types of sensor elements is also possible, for example to sensor elements with tape-like test elements, for example as set forth in EP 0 299 517 B1.

The test element comprises a proximal end and a distal end, analogously to the design of the lancet in the above-described medical aid, although in principle each area of the test element can be defined as proximal end or distal end.

The proximal end and the distal end of the test element are preferably arranged on mutually opposite sides of the test element. The test element can in particular comprise an active surface that serves for the detection of the at least one analyte. For example, this active surface can comprise one or more test areas which, for example, have a detection chemical for detection of the at least one analyte. As has been described above, this detection can be performed electrochemically and/or optically. The active surface of the at least one test element is preferably arranged in the region of the proximal end of the test element. However, the active surface of the test element can also remain completely or partially outside the packaging, particularly if, as has been described above, sample fluid is delivered to this active surface. However, the proximal end of the test element (and thus the packaged part of the test element) should include the implantable parts of the test element and/or other component parts of the sensor that are implanted.

Analogously to the lancet tip of the medical aid, the test element is at least partially enclosed by a packaging. As has been explained above, one or more test elements can be received in the packaging. In addition to the actual test element that serves for the detection of the at least one analyte, it is also possible, as has been described above, for other elements to be received in the packaging, for example component parts of an insertion aid for an implantable test element, in particular component parts that are at least temporarily implanted.

As regards the design of the packaging, which constitutes the basic concept of the invention, reference may be made to the above description. All the embodiments of the packaging that have been described in connection with the medical aid are applicable analogously in the context of the proposed sensor.

Thus, the packaging comprises at least one flexible film section having a distal end, a proximal end, a first lateral edge and a second lateral edge. Moreover, the test element, at least partially enclosed by the packaging, is arranged displaceably between an upper protective section and a lower protective section, wherein the at least one flexible film section is detachably connected, along at least one segment of its first and second lateral edges, to an additional flexible film section or to one of the protective sections. Moreover, the at least one flexible film section is connected to an additional flexible film section or to one of the protective sections in the area of the proximal end of the test element via a detachable connection, such that the proximal end of the test element is enclosed by the packaging. The at least one flexible film section is connected to one of the protective sections via a fixed connection at a distance from the detachable connection. The proximal ends of the lower and upper protective sections can be bent apart, as a result of which the distance between the detachable connection and the fixed connection can be increased and a tensile force can thus be applied to the detachable connection, such that the packaging is opened at the detachable connection and a proximal opening is created through which at least part of the test element can be pushed out from the packaging in the proximal direction.

For other possible embodiments of the sensor, reference may be made to the above description of the possible embodiments of the medical aid. In doing so, the lancet is to be replaced in each case by the test element, and the lancet tip in each case by the proximal end of the test element. The stated advantages of the packaging can also be transposed analogously to the advantages of the packaging of the sensor.

BRIEF DESCRIPTION OF THE DRAWINGS

The invention is explained in more detail below with reference to the drawing, in which.

DESCRIPTION OF THE SELECTED EMBODIMENTS

Figure 1:
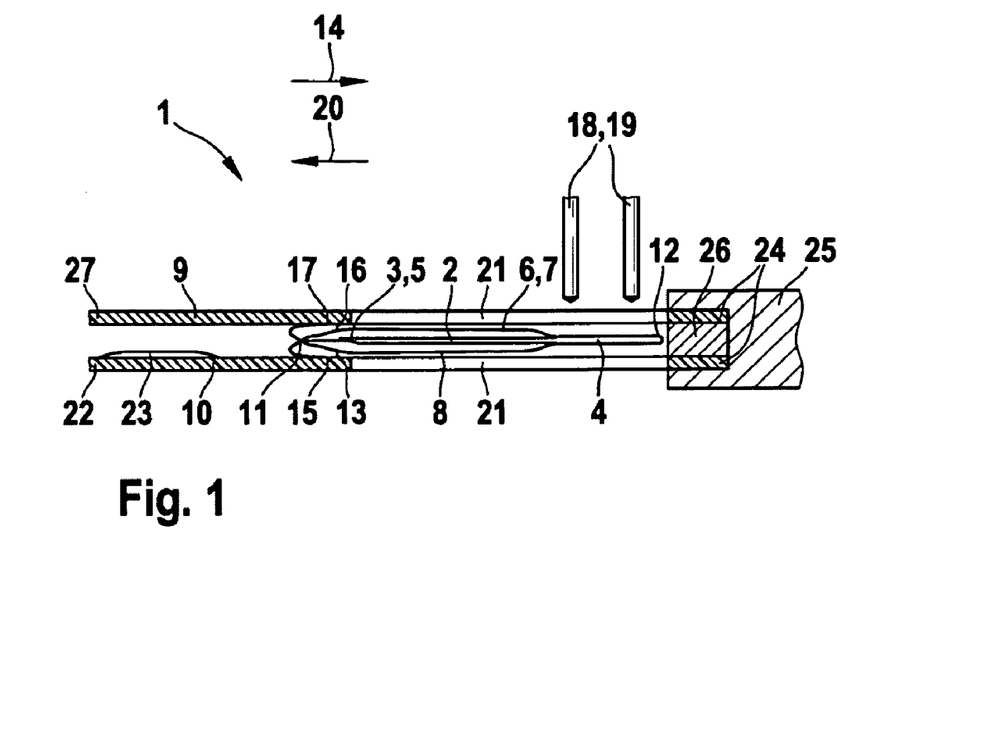
FIG. 1 shows a schematic cross section through a medical aid according to the invention before use, with the flexible packaging unopened.

FIG. 1 shows a schematic view of a preferred embodiment of a medical aid according to the invention, before the flexible packaging is opened.

The medical aid 1 comprises a lancet 2 with a lancet tip 3 and a lancet body 4. The lancet tip 3 is arranged at the proximal end 5 of the lancet 2. The lancet 2 is enclosed by a flexible packaging 6. The flexible packaging 6 has an upper flexible film section 7 and a lower flexible film section 8. These flexible film sections 7, 8 are detachably connected to each other along their lateral edges (not shown). In front of the lancet tip 3, the flexible film sections 7, 8 are detachably connected to each other via a proximal seam 11. The upper and lower flexible film sections 7, 8 are sections of a single flexible film which, at the distal ends 12 of the flexible film sections 7, 8, is bent back round the distal end of the lancet body 4. The distal end of the lancet body 4 is adhesively bonded into the flexible packaging 6. The lancet 2 is arranged displaceably between an upper protective section 9 and a lower protective section 10. The proximal end 13 of the lower flexible film section 8 is connected fixedly to the lower protective section 10 at the first connection site 15, the proximal end 13 of the lower flexible film section 8 being bent in the distal direction 14 to the first connection site 15 relative to the proximal seam 11. The proximal end 16 of the upper flexible film section 7 is connected to the upper protective section 9 at the second connection site 17, the proximal end 16 of the upper flexible film section 7 being bent back in the distal direction 14 to the second connection site 17 relative to the proximal seam 11.

The lancet 2 has a capillary structure (not shown) which is formed by a half-open channel and which can take up a sample by means of capillary forces.

In the embodiment shown, two pins 19 are provided as the driver element 18 and can engage in two holes in the lancet body 4 in order to be able to displace the lancet 2 in the proximal direction 20. The driver element 18 can be connected to the lancet 2 just shortly before the displacement of the lancet 2. It is preferably driven by a component of a drive system (not shown) in order to automatically displace the lancet 2 first in the proximal direction 20 and, after use, back in the distal direction 14. The upper and lower protective sections 9, 10 are provided with slit-shaped recesses 21 through which the driver element 18 slides and is guided during its displacement.

The two protective sections 9, 10 extend beyond the flexible packaging 6 in the proximal direction 20. The proximal end 22 of the lower protective section 10 has, on its inside, a test area 23 provided for analysis of a sample.

The distal ends 24 of the protective sections 9, 10 are connected to a holding element 25, which comprises a spacer piece 26 by means of which the protective sections 9, 10 are held at a defined distance from each other. The spacer piece 26 can be made, for example, from a piece of thick plastic film and can be secured between the distal ends 24 of the protective sections 9, 10 before these are received by the holding element 25.

Figure 2:
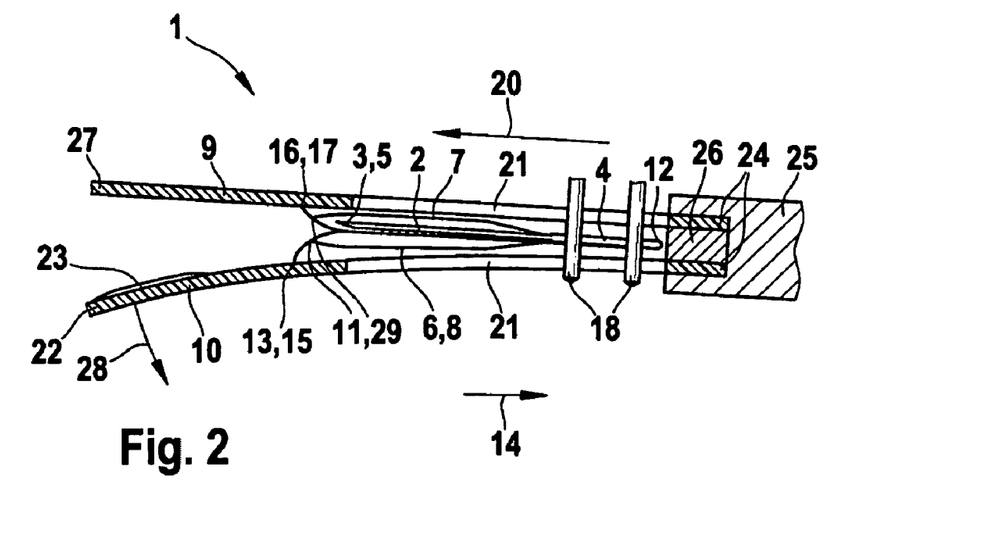
FIG. 2 shows a schematic cross section through a medical aid according to the invention from FIG. 1, after the flexible packaging has been opened.

FIG. 2 shows the medical aid from FIG. 1 and serves to explain the use of the medical aid.

To unpack the medical aid 1, the proximal ends 22, 27 of the protective sections 9, 10 are bent apart, for example by bending the proximal end 22 of the lower protective section 10 in the direction of bending 28. In this way, the proximal ends 13, 16 of the flexible film sections 8, 7 are pulled apart, on account of their fixed connection to the protective sections 10, 9 at the connection sites 15, 17, such that the detachable connection at the proximal seam 11 comes undone, as a result of which a proximal opening 29 is created.

By means of the driver element 18, the lancet 2 can then be pushed in the proximal direction 20 through the proximal opening 29 and (without scratching the test area 23) out from the protective sections 9, 10, such that at least the lancet tip 3 protrudes beyond the proximal ends 22, 27 of the protective sections 10, 9. In this position, the lancet tip can be inserted into the skin of a user, and the sample thereby obtained (blood or interstitial fluid) can then be taken up into the capillary structure of the lancet 2. By pushing the lancet 2 out from the flexible packaging 6, the latter may be opened still further, for example along the lateral edges of the flexible film sections 7, 8.

After the skin has been punctured and the sample collected, the capillary structure of the lancet 2, now filled with the sample, is pulled back in the distal direction 14 as far as the level of the test area 23 by means of the driver element 18. The sample is then stripped off the lancet 2 onto the test area 23 when, by means of the proximal end 22 of the lower protective section 10 being bent back counter to the direction of bending 28, the test area 23 is brought into contact with the lancet 2 at a defined time.

Figure 3:
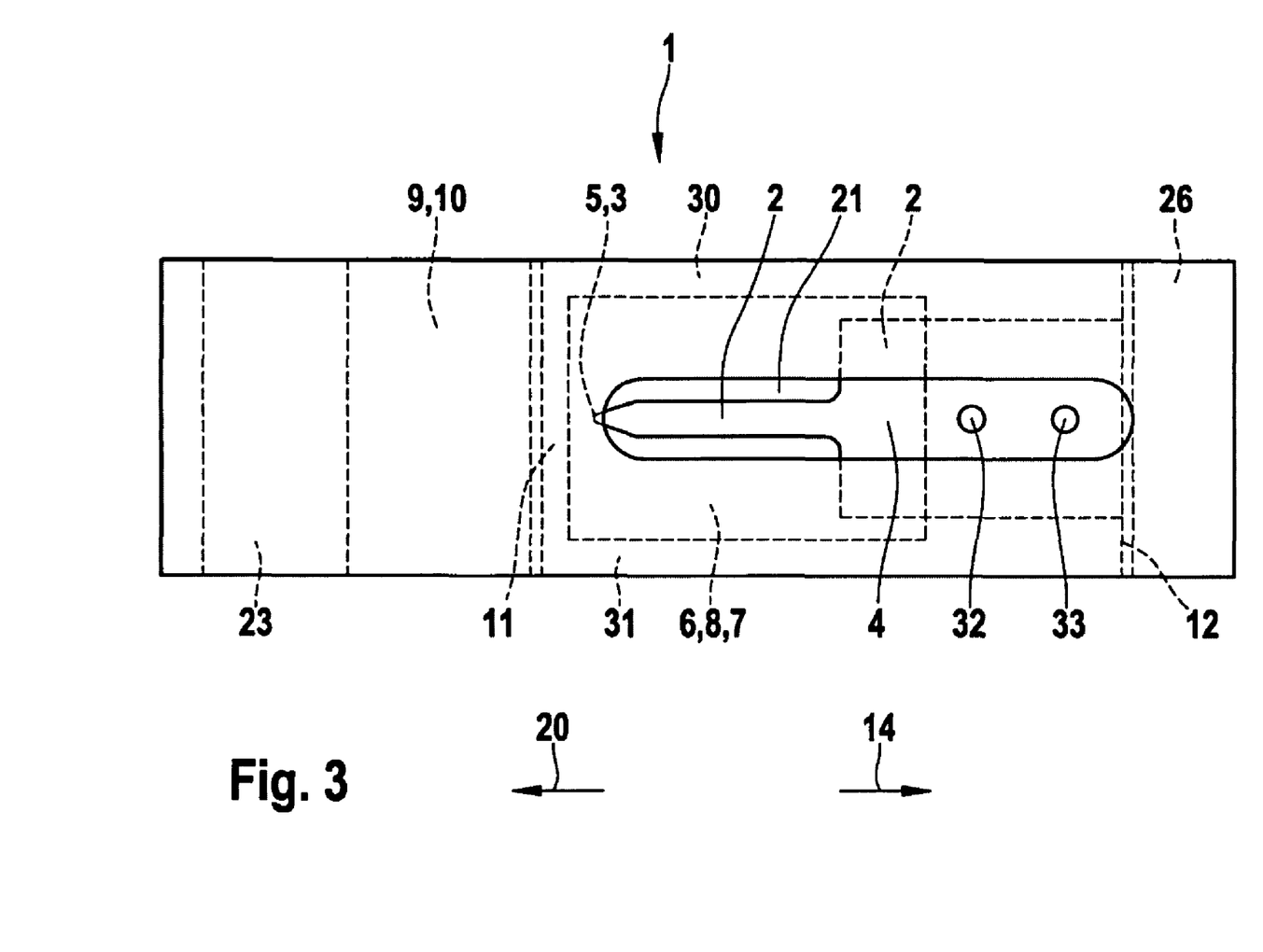
FIG. 3 shows a schematic plan view of a medical aid according to the invention, with the flexible packaging unopened.

FIG. 3 shows a schematic plan view of a preferred embodiment of a medical aid according to the invention, before the flexible packaging is opened.

The medical aid 1 comprises a lancet 2 with a lancet tip 3 and a lancet body 4. The lancet tip 3 is arranged at the proximal end 5 of the lancet 2. The lancet 2 is enclosed by a flexible packaging 6. The flexible packaging 6 has an upper flexible film section 7 and a lower flexible film section 8.

These flexible film sections 7, 8 are detachably connected to each other along their lateral edges 30, 31. In front of the lancet tip 3, the flexible film sections 7, 8 are detachably connected to each other via a proximal seam 11. The upper and lower flexible film sections 7, 8 are sections of a single flexible film which, at the distal ends 12 of the flexible film sections 7, 8, are bent back round the distal end of the lancet body 4. The distal end of the lancet body 4 is adhesively bonded into the flexible packaging 6. The lancet 2 is arranged displaceably between an upper protective section 9 and a lower protective section 10. The proximal end of the lower flexible film section 8 is connected fixedly to the lower protective section 10 at the first connection site. The proximal end 16 of the upper flexible film section 7 is connected fixedly to the upper protective section 9 at the second connection site.

The lancet 2 has a capillary structure (not shown) which is formed by a half-open channel and which can take up a sample by means of capillary forces.

In the embodiment shown, two pins (not shown) are provided as the driver element 18 and can engage in two holes 32, 33 in the lancet body 4 in order to be able to displace the lancet 2 in the proximal direction 20. The driver element 18 can be connected to the lancet 2 just shortly before the displacement of the lancet 2. The upper and lower protective sections 9, 10 are provided with slit-shaped recesses 21 through which the driver element 18 slides and is guided during its displacement.

The two protective sections 9, 10 extend beyond the flexible packaging 6 in the proximal direction 20. The proximal end 22 of the lower protective section 10 has, on its inside, a test area 23 provided for analysis of a sample.

The distal ends 24 of the protective sections 9, 10 are connected to a holding element (not shown) via the spacer piece 26. The spacer piece 26 holds the protective sections 9, 10 at a defined distance from each other. The spacer piece 26 can be made, for example, from a piece of thick plastic film and can be secured between the distal ends 24 of the protective sections 9, 10 before these are received by the holding element 25.

The above illustrative embodiments in FIGS. 1 to 3 show an example of a medical aid 1 according to the invention. It will be noted that these illustrative embodiments can also be transposed analogously to a sensor according to the invention. Therefore, to make matters simpler, illustrative embodiments with a sensor instead of a medical aid are not shown. In these illustrative embodiments, the lancet 2 in FIGS. 1 to 3 would be replaced analogously by a test element, for example one of the test elements mentioned in the prior art, and the lancet tip 3 would correspond to the proximal end of the test element. In other respects, the illustrative embodiments are analogous.

LIST OF REFERENCE NUMBERS 1 medical aid
2 lancet
3 lancet tip
4 lancet body
5 proximal end of lancet
6 flexible packaging
7 upper flexible film section
8 lower flexible film section
9 upper protective section
10 lower protective section
11 proximal seam
12 distal ends of the flexible film sections
13 proximal end of lower flexible film section
14 distal direction
15 first connection site
16 proximal end of upper flexible film section
17 second connection site
18 driver element
19 pins
20 proximal direction
21 recesses
22 proximal end of lower protective section
23 test area
24 distal ends of the protective sections
25 holding element
26 spacer piece
27 proximal end of upper protective section
28 direction of bending
29 proximal opening
30 first lateral edge
31 second lateral edge
32 first hole
33 second hole

The invention claimed is:

1. A medical aid comprising a lancet with a proximal end and a distal end, the lancet having a lancet body and, at the proximal end, a lancet tip, and the lancet being at least partially enclosed by a packaging that comprises:
at least one flexible film section having a distal end, a proximal end, a first lateral edge and a second lateral edge, wherein the lancet, at least partially enclosed by the packaging, is arranged displaceably between an upper protective section and a lower protective section, wherein the at least one flexible film section is detachably connected, along at least one segment of its first and second lateral edges, to an additional flexible film section or to one of the protective sections, and wherein the at least one flexible film section is connected to an additional flexible film section or to one of the protective sections in the area of the lancet tip via a detachable connection, such that the lancet tip is enclosed by the packaging, and wherein the at least one flexible film section is connected to one of the protective sections via a fixed connection at a distance from the detachable connection, and wherein the proximal ends of the lower and upper protective sections can be bent apart, as a result of which the distance between the detachable connection and the fixed connection can be increased and a tensile force can thus be applied to the detachable connection, such that the packaging is opened at the detachable connection and a proximal opening is created through which at least part of the lancet can be pushed out from the packaging in the proximal direction relative to the lower and upper protective sections.

2. The medical aid as claimed in claim 1, wherein the lancet is at least partially enclosed by a flexible packaging which comprises an upper flexible film section having a distal end, a proximal end, a first lateral edge and a second lateral edge, and a lower flexible film section having a distal end, a proximal end, a first lateral edge and a second lateral edge, wherein the upper and lower flexible film sections are detachably connected to each other along at least one segment of their first and second lateral edges and at least partially enclose the lancet, wherein the lower flexible film section and the upper flexible film section are detachably connected to each other via a proximal seam in front of the lancet tip, and the lancet tip is thus enclosed by the flexible packaging, and wherein the proximal end of the lower flexible film section is fixedly connected to the lower protective section and the proximal end of the upper flexible film section is fixedly connected to the upper protective section, and the proximal ends of the lower and upper protective sections can be bent apart in order to open the flexible packaging at the proximal seam, whereupon at least part of the lancet can be pushed out from the flexible packaging and from the protective sections in the proximal direction.

3. The medical aid as claimed in claim 2, wherein the upper and lower flexible film sections are sections of a single flexible film that is bent back at the distal ends of the flexible film sections.

4. The medical aid as claimed in claim 1, wherein the lancet has a capillary structure formed by a half-open channel.

5. The medical aid as claimed in claim 1, comprising a driver element which engages through at least one of the protective sections, is connected to the lancet body and can be displaced together with the lancet in the proximal direction.

6. The medical aid as claimed in claim 5, wherein at least one of the protective sections has a recess through which the driver element slides and is guided during its displacement.

7. The medical aid as claimed in claim 1, wherein the distal end of the lancet body is adhesively bonded into the packaging.

8. The medical aid as claimed in claim 1, wherein the proximal end of one of the protective sections has, on its inside, a test area, which is provided for analysis of a sample.

9. The medical aid as claimed in claim 1, wherein the distal ends of the protective sections are connected to a holding element that comprises a spacer piece, by means of which the distal ends of the protective sections are held at a defined distance from each other.

10. A method for unpacking the medical aid as claimed in claim 1, further comprising:

bending the proximal ends of the lower and upper protective sections apart, as a result of which the packaging is opened at the detachable connection, such that the proximal opening is created, and pushing at least part of the lancet out from the packaging and from the protective sections in the proximal direction through the proximal opening, such that at least the lancet tip protrudes beyond the proximal ends of the protective sections.

11. The use of the medical aid as claimed in claim 1 for taking up a sample on a test area arranged on the inside at the proximal end of one of the protective sections, by means of the sample being taken up in a capillary structure formed by a half-open channel of the lancet and by means of the sample being scraped off onto the test area.

12. A sensor for detection of at least one analyte in a sample, in particular for detection of glucose in a blood sample or in interstitial fluid, comprising:

at least one test element with a proximal end and a distal end, the test element being at least partially enclosed by a packaging that comprises at least one flexible film section having a distal end, a proximal end, a first lateral edge and a second lateral edge, wherein the test element, at least partially enclosed by the packaging, is arranged displaceably between an upper protective section and a lower protective section, wherein the at least one flexible film section is detachably connected, along at least one segment of its first and second lateral edges, to an additional flexible film section or to one of the protective sections, and wherein the at least one flexible film section is connected to an additional flexible film section or to one of the protective sections in the area of the proximal end of the test element via a detachable connection, such that the proximal end of the test element is enclosed by the packaging, and wherein the at least one flexible film section is connected to one of the protective sections via a fixed connection at a distance from the detachable connection, and wherein the proximal ends of the lower and upper protective sections can be bent apart, as a result of which the distance between the detachable connection and the fixed connection can be increased and a tensile force can thus be applied to the detachable connection, such that the packaging is opened at the detachable connection and a proximal opening is created through which at least part of the test element can be pushed out from the packaging in the proximal direction relative to the lower and upper protective sections.

* * * * *